United States Patent [19]
Pollock et al.

[11] 3,959,120
[45] May 25, 1976

[54] APPARATUS FOR PREPARING FERMENTED LIQUIDS

[75] Inventors: James Richard Allen Pollock; Michael Joseph Weir, both of Reading, England

[73] Assignee: James R. A. Pollock, England

[22] Filed: Mar. 4, 1974

[21] Appl. No.: 447,682

[52] U.S. Cl............................ 195/141; 195/142; 195/134; 99/276
[51] Int. Cl.² ........................................ C12B 1/00
[58] Field of Search ........... 195/140, 141, 142, 134; 99/276

[56] References Cited
UNITED STATES PATENTS

| | | | |
|---|---|---|---|
| 963,458 | 7/1910 | Moeller | 99/276 |
| 1,948,836 | 2/1934 | Ash | 195/142 |
| 3,801,468 | 4/1974 | Lumb et al. | 195/141 |

*Primary Examiner*—Alvin E. Tanenholtz
*Attorney, Agent, or Firm*—Larson, Taylor and Hinds

[57] ABSTRACT

This invention relates to apparatus for fermenting liquid particularly on a domestic scale, the apparatus comprising a first and a second chamber, the said first chamber having a support for yeast, a closable inlet for charging said first chamber with liquid to be fermented and a gas outlet to which is attached a valve the first said chamber being connected in series with the second said chamber for liquid flow, the second said chamber having a closable outlet for liquid and a gas outlet to which is attached a valve.

3 Claims, 1 Drawing Figure

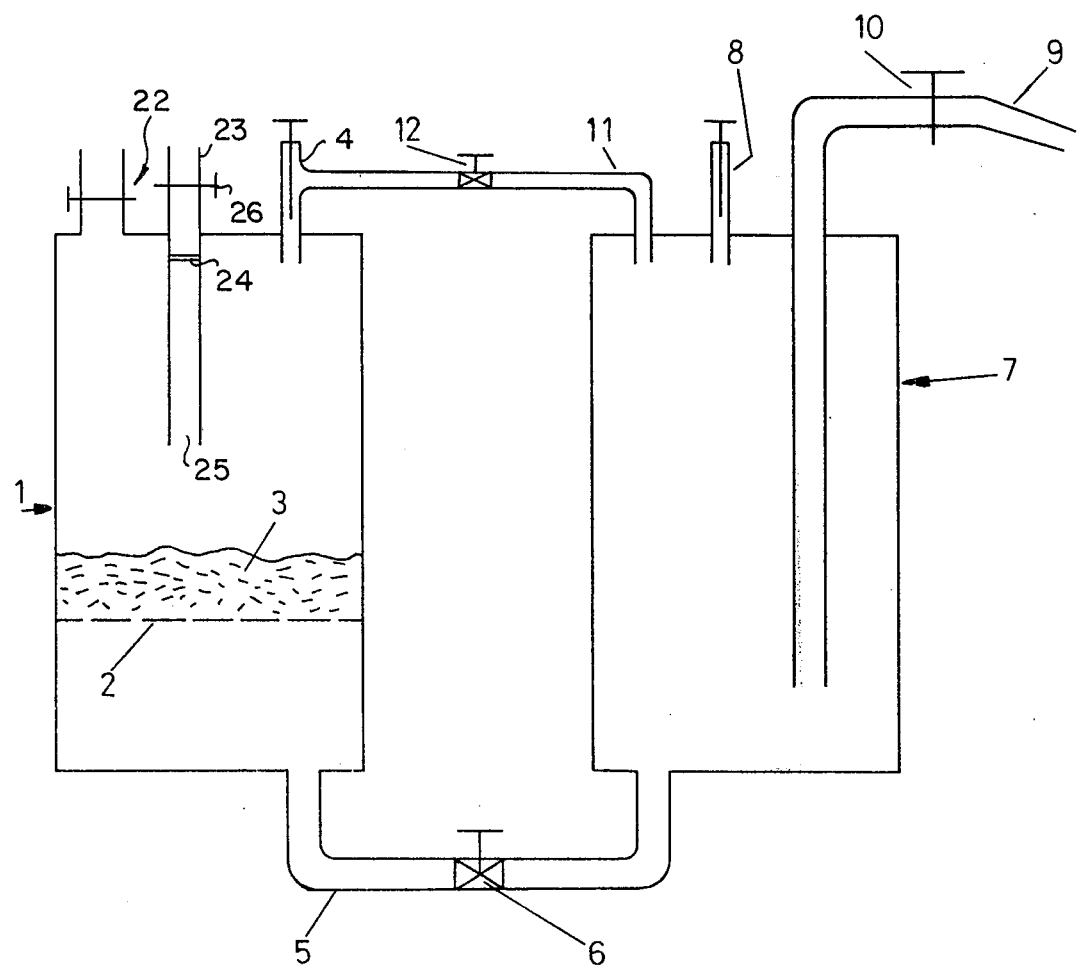

APPARATUS FOR PREPARING FERMENTED LIQUIDS

This invention relates to apparatus for the rapid fermentation of liquids on a small scale, more particularly for continuous fermentation and for fermentation of suspensions.

In apparatus for use in conventional fermentation techniques of the type wherein yeast is allowed to separate by sedimentation or flotation, long in use for fermenting liquids on a scale small enough for domestic use, separate units are necessary for the operations of separating off yeast and saturation of the product with carbon dioxide at atmospheric pressure. A separate unit is used for carbonation in excess of saturation at atmospheric pressure, for example a secondary fermentation apparatus or apparatus for adding carbon dioxide externally. Such apparatus may, for example, be used for producing beer and comprise a separate unit or units for clarifying the beer, after separation of the yeast, by finings and/or filtration; or for producing wine. A fermentation process of the above-indicated kind generally lasts for several days and the several above-indicated separate operations lead to a great chance of spoilage of the products, possibly after excess carbonation, by oxidation, and/or the bacterial action of undesirable microorganisms introduced into the product, or a combination thereof.

The present invention provides apparatus for the rapid production on a small scale, of a clear fermented liquid saturated with carbon dioxide gas at any desired pressure by which the number of separate units is reduced and thereby the risk of spoilage is reduced.

It has been found that apparatus according to the present invention is not limited in its effective utilization to small-scale operation.

According to the invention, apparatus is provided for preparing a fermented liquid essentially free of yeast which comprises a first, fermentation chamber for receiving a charge of fermentable liquid, filter aid material and yeast, said chamber including means permeable to liquid for retaining the yeast and filter aid material within the first chamber; a second, storage chamber for receiving fermented and filtered liquid and including a closable outlet for the fermented and filtered liquid; a closable passage for directly connecting the first chamber to the second chamber so as to provide a flow of liquid, which has been fermented and filtered in the first chamber, from the first chamber to the second chamber; and means for independently controlling the gas pressure in each chamber to enable the first chamber to be at a higher pressure than the second chamber.

In the apparatus according to the invention, the first chamber may be an upward continuation of the second chamber and separated from it by a zone comprising the means for supporting the yeast or the cake of yeast and filter aid; or, preferably, the chambers are separate vessels and are connected to each other by a tube along which the fermented liquid can flow. It is also preferred that there is a detachably secured connecting means from the valve of the first chamber to the second chamber so that gas discharge from the first chamber can be introduced into the second chamber.

According to an example of a method of utilising the apparatus, a cake of yeast and filter aid is placed on the support for it in the first chamber, and a fermentable liquid is charged to the first chamber, which is closed. The first chamber is connected by a closed passage, to the second chamber. An open passage connects the gas port of the valve of the first chamber to an inlet on the upper part of the second chamber or to the valve of the second chamber. The second chamber valve is set to operate at a pressure equal to that at which the valve on the first chamber operates. The outlet for removal of the liquid from the second chamber is closed.

It will be readily understood that carbon dioxide formed during the fermentation escapes from the fermentation zone and so raises the pressure in the first chamber, eventually to the level at which gas passes the pressure-regulation valve. This gas passes on into the second chamber and eventually raises the pressure there to that at which the pressure-regulating valve in it operates. When the fermentation has reached this stage, the passage connecting the first vessel with the second is opened and the operating pressures are adjusted so that the pressure in the second chamber is lower than in the first. Under these conditions there is a slow flow of filtered fermented liquid into the second chamber. When substantially all the liquid has been collected in the second chamber, it may be dispensed for consumption or further treatment, for instance for admixture with flavouring substances. It will be understood that the fermentation agent must be renewed from time to time and that various fermenting agents, e.g. various yeasts, can be used according to the product desired.

The following is a description of an example of apparatus according to the invention made with reference to the accompanying drawing: a first chamber 1 has a support or retaining means 2 for yeast or a cake of yeast and inert filter material 3, a valve 4 for control of the gas pressure in the chamber and an inlet 22. Tube 5 connecting chamber 1 with chamber 7 has valve 6 for controlling the flow of filtered and fermented liquid. Chamber 7 has a valve 8 for regulation of the gas pressure, and an outlet 9, for removal of the fermented liquid, which can be closed at 10.

Valve 4 is connected to chamber 7 by tube 11 and the flow of gas can be controlled by a valve 12.

The apparatus of the invention may include means to enable material to be held in a chamber in order to be contacted under predetermined conditions by liquid in the chamber. The means comprises a further small chamber or compartment in the first chamber having an opening in the lower end normally below liquid level, means to permit and control the escape of gas from the further chamber and means to retain material in the compartment.

The foregoing may be implemented as shown in the drawing wherein the compartment comprises a tube 23 attached to the first chamber 1 and having the lower end 25 open and normally below liquid level. In the tube 23 is a permeable support 24, e.g. a porous plug for sugar. The top of the tube 23 may be flush with or protrude from the top of the chamber as illustrated and has a gas valve 26 located therein.

In practice as fermentation proceeds the gas pressure builds up in the chamber 1 and when sugar is required to be dissolved in the liquid, gas is allowed to escape from the tube 23 by opening valve 26. The pressure difference forces liquid up the tube 23 and through the plug 24 to contact the sugar.

We claim:
1. Apparatus for preparing a fermented liquid essentially free of yeast comprising a first, fermentation chamber for receiving a charge of fermentable liquid, filter aid material and yeast, said first chamber including means permeable to liquid for filtering the liquid and retaining the yeast and filter aid material within said first chamber; a second, storage chamber for receiving fermented and filtered liquid and including a closable outlet for the fermented and filtered liquid; a closable passage directly connecting said first chamber to the second chamber so as to provide for a flow of liquid, which has been fermented and filtered in the first chamber, from the first chamber to the second chamber; and means for independently controlling the gas pressure in each chamber to enable the first chamber to be at a higher pressure than the second chamber, including a pressure regulating valve associated with the first chamber, the outlet of said pressure regulating valve being connected to the second chamber for passage of gas from a level above the normal liquid level in the first chamber to the second chamber.

2. Apparatus according to claim 1 wherein the first chamber includes a compartment which includes an opening in the lower end thereof that is normally below the liquid level in the chamber, means for controlling the escape of gas from the first chamber through the compartment, and means for retaining material in the compartment at a level normally above the liquid level such that liquid which is caused to rise up in the compartment will contact the material.

3. Apparatus according to claim 2 in which the compartment comprises a tube, said means for controlling the escape of gas comprising a valve associated with said tube and said material retaining means comprising a porous plug.

* * * * *